United States Patent
Stewart et al.

(10) Patent No.: US 8,574,851 B2
(45) Date of Patent: Nov. 5, 2013

(54) PREDICTION AND PREVENTION OF PREECLAMPSIA

(75) Inventors: Dennis Stewart, Los Gatos, CA (US); Kirk P. Conrad, Gainesville, FL (US); Arundhathi Jeyabalan, Pittsburgh, PA (US)

(73) Assignees: Corthera, Inc., San Mateo, CA (US); University of Pittsburgh-Of the Commonwealth System of Higher Education, Pittsburgh, PA (US); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/129,597

(22) PCT Filed: Nov. 24, 2009

(86) PCT No.: PCT/US2009/065795
§ 371 (c)(1),
(2), (4) Date: Jul. 29, 2011

(87) PCT Pub. No.: WO2010/060102
PCT Pub. Date: May 27, 2010

(65) Prior Publication Data
US 2011/0281801 A1    Nov. 17, 2011

Related U.S. Application Data

(60) Provisional application No. 61/200,150, filed on Nov. 24, 2008.

(51) Int. Cl.
*G01N 33/53* (2006.01)
*A61K 38/22* (2006.01)

(52) U.S. Cl.
USPC .......................................... 435/7.1; 514/12.7

(58) Field of Classification Search
None
See application file for complete search history.

(56) References Cited

U.S. PATENT DOCUMENTS 7,553,813 B2 *  6/2009  Unemori ........................ 514/1.1
2008/0108572 A1  5/2008  Unemori

OTHER PUBLICATIONS

Lafayette et al., Clinical Nephrology, 75(3):226-232, 2011.*
Szlachter et al., Obstetrics and Gynecology, 59:167-170, 1982.*
Conrad, Seminars in Nephology, 31(1):15-32, 2011, doi:10.1016/j.semnephrol.2010.10.003.*
Novak, J. et al., "Relaxin is essential for renal vasodilation during pregnancy in conscious rats", The Journal of Clinical Investigation, vol. 107, No. 11, pp. 1469-1475, 2001.
Decker et al., "Some effects of relaxin in obstetrics", Obstet Gynecol 1958, 12(1):37-46.
Spencer et al., First-trimester maternal serum PP-13, PAPP-A and second-trimester uterine artery Doppler pulsatility index as markers of pre-eclampsia. Ultrasound Obstet Gynecol 2007, 29: 128-134.
Ness et al., Heterogeneous causes constituting the single syndrome of preeclamsia: a hypothesis and its implications: Am J Obstet Gynecol 1996, 175:1365-70.
Qiu et al., A prospective study of maternal serum C-reactive protein concentrations and risk of preeclampsia Am J Hypertens 2004, 17:154-160.
Hwang, et al. Maternal serum highly sensitive C-reactive protein in normal pregnancy and preeclampsia. International Journal of Gynecology and Obstetrics 2007, 98: 105-109.
Stewart, Dennis R et al.The relationship between hCG and relaxin secretion in normal pregnancies vs peri-implantation spontaneous abortions, Clinical Endocrinology, vol. 38, pp. 379-385, 1993.
Kumru, S. et.al., 2006, "Correlation of maternal serum high-sensitive C-reactive protein levels with biochemical and clinical parameters in preeclampsia", Eur Journal Obstet Gynecol Reprod Bioi, Feb. 2006, vol. 124, No. 2, pp. 164-167.
Unemori Elaine et al: "Scientific rationale and design of a Phase I safety study of relaxin in women with severe preeclampsia", Prelaxin ,and Related Peptides: Fifth lnternational Conference, Ann NY Acad Sol, 1160:381-384, 2009.
Patten Ian S. et al: "Cardiac angiogenic imbalance leads to peripartum cardiomyopathy", Nature, vol. 485 pp. 333-339 May 17, 2012.
Jeyabalan Arun et al: "Low relaxin concentrations in the first trimester are associated with increased risk of developing preeclampsia", Reproductive Sciences vol. 16, No. 3 p. 101A, abstract 113, Mar. 2009.
Davison John M. et al: "New aspects in the pathophysiology of preeclampsia", Journal of the American Society of Nephrology, 15:2440-2448, 2004.

* cited by examiner

Primary Examiner — Marianne P Allen
(74) Attorney, Agent, or Firm — Lisa Matovcik

(57) ABSTRACT

The present disclosure relates to methods for detecting an increased risk of preeclampsia, determining the presence of preeclampsia, reducing the likelihood that preeclampsia will develop and treating preeclampsia. It also provides methods of measuring relaxin levels in a biological sample of a pregnant woman.

5 Claims, 6 Drawing Sheets

PREDICTION AND PREVENTION OF PREECLAMPSIA

RELATED APPLICATIONS

This application is a 371 of PCT/US2009/065795 filed on Nov. 24, 2009, which claims benefit of U.S. provisional Application No. 61/200,150 filed on Nov. 24, 2008, the entire disclosures of which are hereby incorporated by reference.

This application claims benefit under 35 U.S.C. 119(e) of U.S. Provisional Patent Application No. 61/200,150, filed Nov. 24, 2008, which is incorporated herein by reference in its entirety for all purposes.

FIELD

The present disclosure relates to methods for assessing increased risk of preeclampsia in a pregnant woman. The methods described herein employ measuring relaxin levels, and optionally measuring C-reactive protein levels in a biological sample of a pregnant woman. The disclosure further encompasses methods of reducing risk of preeclampsia through administration of a pharmaceutical formulation of relaxin to a pregnant woman.

BACKGROUND

Preeclampsia (also known as toxemia) is a life-threatening condition that affects pregnant women, usually late in the second or third trimester, and postnatal women in the first six weeks after delivery. It is diagnosed by new onset protein in the urine (proteinuria) and high blood pressure. The condition affects the kidneys, liver, brain, heart and placenta of the pregnant woman. Preeclampsia occurs in approximately eight to ten percent of pregnancies and is only alleviated by ending the pregnancy, either by induction of labor or cesarean. Its cause is still largely unknown. Preeclampsia most commonly occurs during a first pregnancy. The risk for preeclampsia is also known to be moderately increased for certain groups of pregnant women, including women who are over 35 years of age or under 18 years of age; women who are genetically predisposed to this condition; women who suffer from preexisting hypertension, diabetes, autoimmune diseases like lupus, various inherited thrombophilias like Factor V Leiden, or renal disease; obese women, and in women with multiple gestations (twins, triplets, and more). The single most significant risk for developing preeclampsia is having had preeclampsia in a previous pregnancy.

Although preeclampsia usually develops after the twentieth week of pregnancy, it can also begin earlier, if there is a hydatiform mole. Preeclampsia can develop either gradually or suddenly, and may remain mild throughout the pregnancy or become severe. Common symptoms in addition to high blood pressure and proteinuria are elevated uric acid, vision problems such as blinking lights or blurry vision, persistent headaches, extreme swelling of hands and feet, fluid retention, pain in the upper right abdomen. If untreated, preeclampsia can damage the mother's liver or kidneys, deprive the fetus of oxygen, and cause eclampsia (seizures). A pregnant woman with signs of preeclampsia must be closely monitored by a physician. Moderate to severe preeclampsia is often treated in the hospital with bed rest, magnesium sulfate, and medication for high blood pressure. Unfortunately, delivery is still the only true "cure" for preeclampsia. In fact, when a woman has severe preeclampsia or is near term with mild to moderate preeclampsia, delivery is still the best remedy to date. Labor is then started with medication, unless a cesarean section is deemed necessary. Within the first few days following delivery, the mother's blood pressure usually returns to normal, however, with severe preeclampsia, it may take several weeks for blood pressure to return to normal.

Specifically, preeclampsia is diagnosed when a pregnant woman develops high blood pressure (two separate readings taken at least four hours apart of 140/90 mm Hg or more) and 300 mg of protein in a 24-hour urine sample (i.e., proteinuria). Swelling or edema, (especially in the hands and face) was long considered an important sign for a diagnosis of preeclampsia, but in today's medical practice only hypertension and proteinuria are necessary for a diagnosis, because up to 40% of women with normal pregnancy can also have edema. However, pitting edema, i.e., unusual swelling, particularly of the hands, feet, or face, which is notable by leaving an indentation when pressed on, can be significant and must be reported to a physician. Although eclampsia is potentially fatal, preeclampsia may be overtly asymptomatic, or may present with symptoms of typical pregnancy-associated ailments. The epigastric pain, for example, which reflects hepatic involvement and is typical of a severe form of preeclampsia termed the HELLP syndrome (i.e., hemolysis, elevated liver enzymes and low platelets) can easily be confused with heartburn, a very common problem of pregnancy. Presumptive diagnosis of preeclampsia, therefore, is dependent upon coincident preeclamptic features, with definitive diagnosis generally not possible until symptom regression after delivery is observed.

Although advances have been made in the realm of preeclampsia screening, clinicians continue to grapple with optimal strategies to monitor pregnant women who are at risk for preeclampsia. An approach that protects both mother and child from the harmful effects of preeclampsia is desired. The present disclosure addresses this need by providing methods for determining whether a pregnant woman has or is predisposed to preeclampsia.

SUMMARY OF THE PREFERRED EMBODIMENTS

The present disclosure provides methods for assessing risk and reducing likelihood of developing preeclampsia in pregnant women. One major advantage of the present disclosure is that risk of developing preeclampsia can be assessed early during pregnancy so that therapy can be initiated in a timely fashion. Another advantage of the present disclosure is that pregnant women who have been determined to be at increased risk for preeclampsia can be treated with relatively low-levels of relaxin or an agonist thereof, so as to prevent or attenuate preeclampsia. Early administration of relaxin may dramatically reduce the number of pregnancy complications due to preeclampsia in pregnant women who are relatively deficient in H2 relaxin during their first trimester of pregnancy. Since relaxin occurs naturally in pregnant women, treatment with exogenous relaxin should not be accompanied by deleterious side effects. Yet another advantage of the present disclosure is that an enriched population of patients can be selected for research and/or clinical studies to better understand preeclampsia, and disease progression in a subset of pregnant subjects who are predisposed to preeclampsia.

In one aspect, the present disclosure provides a method for assessing the risk of the development of preeclampsia in a pregnant human female, including selecting a pregnant human female in the first trimester of pregnancy, and detecting the level of relaxin protein in the pregnant human female to assess the risk of the development of preeclampsia in the human female. In another aspect, the present disclosure provides a method for assessing the risk of the development of preeclampsia in a pregnant human female, including selecting a pregnant human female in the second trimester of pregnancy, and detecting the level of relaxin protein in the pregnant human female to assess the risk of the development of preeclampsia in the human female. In another aspect, the present disclosure provides a method for assessing the risk of the development of preeclampsia in a pregnant human female, including selecting a pregnant human female prior to manifestation of preeclampsia symptoms, and detecting the level of relaxin protein in the pregnant human female to assess the risk of the development of preeclampsia in the human female. Relaxin can be detected in the blood. Preferably, relaxin is detected by using an antibody to relaxin, such as a monoclonal antibody or a polyclonal antibody. In one embodiment of the disclosure, the human female has been pregnant for 5 to 14 weeks. In another embodiment of the disclosure, the human female has been pregnant for 5 to 28 weeks. In another embodiment of the disclosure, the human female is pregnant with more than one child. In another embodiment of the disclosure, the pregnant human female is over 35 years of age of age. In yet another embodiment, the pregnant human female is no more than 18 years of age. In still another embodiment, the pregnant human female is genetically predisposed to preeclampsia. In another aspect of the disclosure, the method further includes detecting the level of C-reactive protein (CRP) in the pregnant human female. CRP is detected in blood. Preferably, CRP is detected by using an antibody to CRP, such as a monoclonal antibody or a polyclonal antibody.

In another aspect, the present disclosure provides a method of reducing the likelihood of the development of preeclampsia in a pregnant human female, including selecting a pregnant human female in the first trimester of pregnancy, wherein the pregnant human female has a level of relaxin of less then about 500 pg/ml in her bloodstream. In another aspect, the present disclosure provides a method of reducing the likelihood of the development of preeclampsia in a pregnant human female, including selecting a pregnant human female in the second trimester of pregnancy, wherein the pregnant human female has a level of relaxin of less then about 500 pg/ml in her bloodstream. In another aspect, the present disclosure provides a method of reducing the likelihood of the development of preeclampsia in a pregnant human female, including selecting a pregnant human female prior to manifestation of preeclampsia symptoms, wherein the pregnant human female has a level of relaxin of less then about 500 pg/ml in her bloodstream. The method further includes administering relaxin in a pharmaceutical formulation to the pregnant human female to reduce the likelihood of developing preeclampsia in the pregnant human female. Relaxin can be administered to the pregnant human female in an amount of about 10 µg/kg to about 100 µg/kg of subject body weight per day. In one preferred embodiment, relaxin is administered to the pregnant human female in an amount of about 30 µg/kg of subject body weight per day. Relaxin administration can begin as soon as the deficiency is noted and can be continued throughout gestation. As such, relaxin is administered to the subject so as to maintain, for example, a serum concentration of relaxin of about 10 ng/ml throughout pregnancy. The pharmaceutical formulation of relaxin can be administered subcutaneously (SQ) or through other routes. For example, relaxin can be delivered via continuous infusion through infusion pumps.

Relaxin employed in the pharmaceutical formulations of the disclosure can be, for example, synthetic or recombinant relaxin, or a pharmaceutically effective relaxin agonist or mimetic. In one embodiment of the disclosure, relaxin is H1 human relaxin. In another embodiment, relaxin is H2 human relaxin. In yet another embodiment, relaxin is H3 human relaxin. In a further embodiment, relaxin is synthetic or recombinant human relaxin, or a pharmaceutically effective relaxin agonist or relaxin mimetic. Thus, the pregnant human female at risk for preeclampsia can be treated with a pharmaceutical formulation of synthetic or recombinant human relaxin or relaxin agonist or mimetic. In one embodiment of the disclosure, the pregnant human female is treated with synthetic human relaxin. In another embodiment, the pregnant human female is treated with recombinant human relaxin. In yet another embodiment, the pregnant human female is treated with a pharmaceutically effective relaxin agonist or mimetic. Relaxin can be administered to the pregnant human female through a number of different routes, including but not limited to, subcutaneously, intramuscularly, intravenously, sublingually and via inhalation. One preferred route of administration is subcutaneous (SQ) administration.

The disclosure further provides relaxin for use in assessing the risk of the development of preeclampsia in a pregnant human female, including selecting a pregnant human female in the first trimester of pregnancy, and detecting the level of relaxin protein in the pregnant human female to assess the risk of the development of preeclampsia in the human female. The disclosure further provides relaxin for use in assessing the risk of the development of preeclampsia in a pregnant human female, including selecting a pregnant human female in the second trimester of pregnancy, and detecting the level of relaxin protein in the pregnant human female to assess the risk of the development of preeclampsia in the human female. The disclosure further provides relaxin for use in assessing the risk of the development of preeclampsia in a pregnant human female, including selecting a pregnant human female prior to manifestation of preeclampsia symptoms, and detecting the level of relaxin protein in the pregnant human female to assess the risk of the development of preeclampsia in the human female. The disclosure further provides relaxin for use in reducing the likelihood of the development of preeclampsia in a pregnant human female, including selecting a pregnant human female in the first trimester of pregnancy, wherein the pregnant human female has a level of relaxin of less then about 500 pg/ml in her bloodstream. The disclosure further provides relaxin for use in reducing the likelihood of the development of preeclampsia in a pregnant human female, including selecting a pregnant human female in the second trimester of pregnancy, wherein the pregnant human female has a level of relaxin of less then about 500 pg/ml in her bloodstream. The disclosure further encompasses relaxin for use in reducing the likelihood of the development of preeclampsia in a pregnant human female, including selecting a pregnant human female prior to manifestation of preeclampsia symptoms, wherein the pregnant human female has a level of relaxin of less then about 500 pg/ml in her bloodstream.

Additionally, the present disclosure provides a method of assessing whether a pregnant woman has an increased risk of developing preeclampsia, comprising: a) measuring H2 relaxin concentration in a biological sample obtained from the pregnant woman prior to manifestation of a preeclampsia symptom; and b) determining that the pregnant woman has an increased risk of developing preeclampsia when the H2 relaxin concentration is less than a cut-off value for a lowest quartile concentration of pregnant women. In some embodiments, the lowest quartile concentration is the H2 relaxin concentration that separates the bottom 25% from the top 75% of H2 relaxin concentrations measured in a group of pregnant women of a similar gestational age and a similar locale. In some embodiments, a similar population of pregnant women of a similar gestational age for the purpose of this disclosure is a population of pregnant women of the same trimester, preferably plus or minus one month gestational age, or more preferably plus or minus two weeks gestational age as the test subject (e.g., pregnant woman of steps a and b). In some embodiments, a similar population of pregnant women of a similar locale for the purpose of this disclosure is a population of pregnant women residing in same continent, same country, preferably within 1000 miles, or more preferably within 500 miles of the test subject (e.g., pregnant woman of steps a and b). In some preferred embodiments, the biological sample comprises plasma or serum. In some preferred embodiments, the H2 relaxin is measured by using an antibody to the H2 relaxin, while is a subset of these embodiments, the H2 relaxin is measured with an enzyme-linked immunosorbant assay (ELISA). In some embodiments, prior to manifestation of a preeclampsia symptom is during the pregnant woman's first trimester that extends from 5 to 15 weeks of pregnancy. The present disclosure also provides methods in which the pregnant woman is part of a group that is predisposed to preeclampsia, the group comprising one or more of a first pregnancy, over 35 years of age, under 18 years of age, multiple gestations, and a pre-existing condition. In some embodiments, the pre-existing condition is selected from the group consisting of hypertension, diabetes, lupus, thrombophilia, renal disease, and obesity. In some preferred embodiments, the cut-off value for a lowest quartile concentration is about 500 pg/ml. Moreover the present disclosure provides methods further comprising measuring C-reactive protein (CRP) concentration in the biological sample, and determining that the pregnant woman has an increased risk of developing preeclampsia when the CRP concentration is greater than about 13.5 mcg/ml, even when the H2 relaxin concentration is greater than about 500 pg/ml. Alternatively the present disclosure provides methods further comprising measuring C-reactive protein (CRP) concentration in the biological sample, and determining that the pregnant woman has an increased risk of developing preeclampsia when the CRP concentration is less than about 1.5 mcg/ml, even when the H2 relaxin concentration is greater than about 500 pg/ml. The present disclosure also provides methods of assessing whether a pregnant woman has preeclampsia, comprising: a) measuring H2 relaxin concentration in a biological sample obtained from the pregnant woman; and b) determining that the pregnant woman has preeclampsia when the H2 relaxin concentration is less than a cut-off value for a lowest quartile concentration of pregnant women. In some preferred embodiments, the biological sample is obtained from the pregnant woman when she has presented with at least one symptom of preeclampsia, and the method is used in part to diagnose the pregnant woman as having preeclampsia. In a subset of these embodiments, the at least one symptom of preeclampsia comprises one or more of the group consisting of edema, severe headache, change in vision, upper abdominal pain, nausea, vomiting, dizziness, decreased urine output, and sudden weight gain of more than two pounds per a week.

Also, the present disclosure provides methods of reducing the likelihood that a pregnant woman will develop preeclampsia, comprising: a) selecting a pregnant woman having a serum H2 relaxation concentration of less then about 500 pg/ml in a biological sample obtained during her first trimester of pregnancy; and b) administering H2 relaxin in a pharmaceutical formulation to the pregnant woman to reduce the likelihood that she will develop preeclampsia. In some embodiments, the H2 relaxin is administered to the pregnant woman in an amount of about 30 μg/kg of body weight per day throughout the terminal part of gestation (e.g., subsequent to determination of the H2 relaxin concentration). In some embodiments, the H2 relaxin is administered to the pregnant woman so as to maintain a serum concentration of relaxin of about 10 ng/ml throughout pregnancy. In preferred methods, the serum H2 relaxin concentration is determined by immunoassay. In some embodiments, the first trimester extends from 5 to 15 weeks of pregnancy. In some embodiments, the pregnant woman is part of a group that is predisposed to preeclampsia, the group comprising one or more of a first pregnancy, over 35 years of age, under 18 years of age, multiple gestations, and a pre-existing condition. In a subset of these embodiments, the pre-existing condition is selected from the group consisting of hypertension, diabetes, lupus, thrombophilia, renal disease, and obesity. In some particularly preferred embodiments, the pregnant woman is from North America. More preferably the pregnant woman is from the industrial northeast region of North America (e.g., within 250 miles of Pittsburgh).

Moreover, the present disclosure provides a monoclonal antibody reactive with H2 relaxin, the monoclonal antibody produced by a hybridoma set forth as American Type Culture Collection (ATCC) PTA-8423. In further embodiments, an immunoassay kit is provided comprising the monoclonal antibody produced by the hybridoma of PTA 8423, a microplate, and instructions for measuring H2 relaxin concentration of a sample. In some preferred embodiments, the immunoassay is a H2 relaxin capture assay, which further comprises a polyclonal anti-relaxin antibody.

DETAILED DESCRIPTION

General Overview

In one aspect, the present disclosure relates to methods for assessing risk of developing preeclampsia in pregnant human subjects. The methods described herein employ measuring the level of relaxin, and optionally C-reactive protein (CRP) in a biological sample obtained from a pregnant woman during her first trimester. Since preeclampsia is one of the primary reasons why women are admitted to the hospital during pregnancy, it is associated with high cost to the health care system. The prognosis for pregnant women who are admitted with preeclampsia or symptoms thereof has so far been dire as preeclampsia often leads to early termination of pregnancy via cesarean section because of maternal or fetal health concerns, especially in cases where the blood pressure of the mother has risen above 140/90 mmHg. As of today there is no cure for preeclampsia other than termination of pregnancy. To mitigate this problem, the present disclosure provides a test that can be used to assess the likelihood or risk of developing preeclampsia. In preferred embodiments, the tests are conducted in early pregnancy (e.g., first trimester) such that women can be monitored and suitable intervention taken to prevent preeclampsia from ever fully developing. The early awareness of a heightened risk of preeclampsia allows the attending physician to stabilize the pregnant patient's condition from the onset. Intervention in the form of therapy to prevent or reduce high blood pressure in turn reduces the risk of mortality of mother and child and further reduces the risk of early termination of pregnancy.

Figure 1:
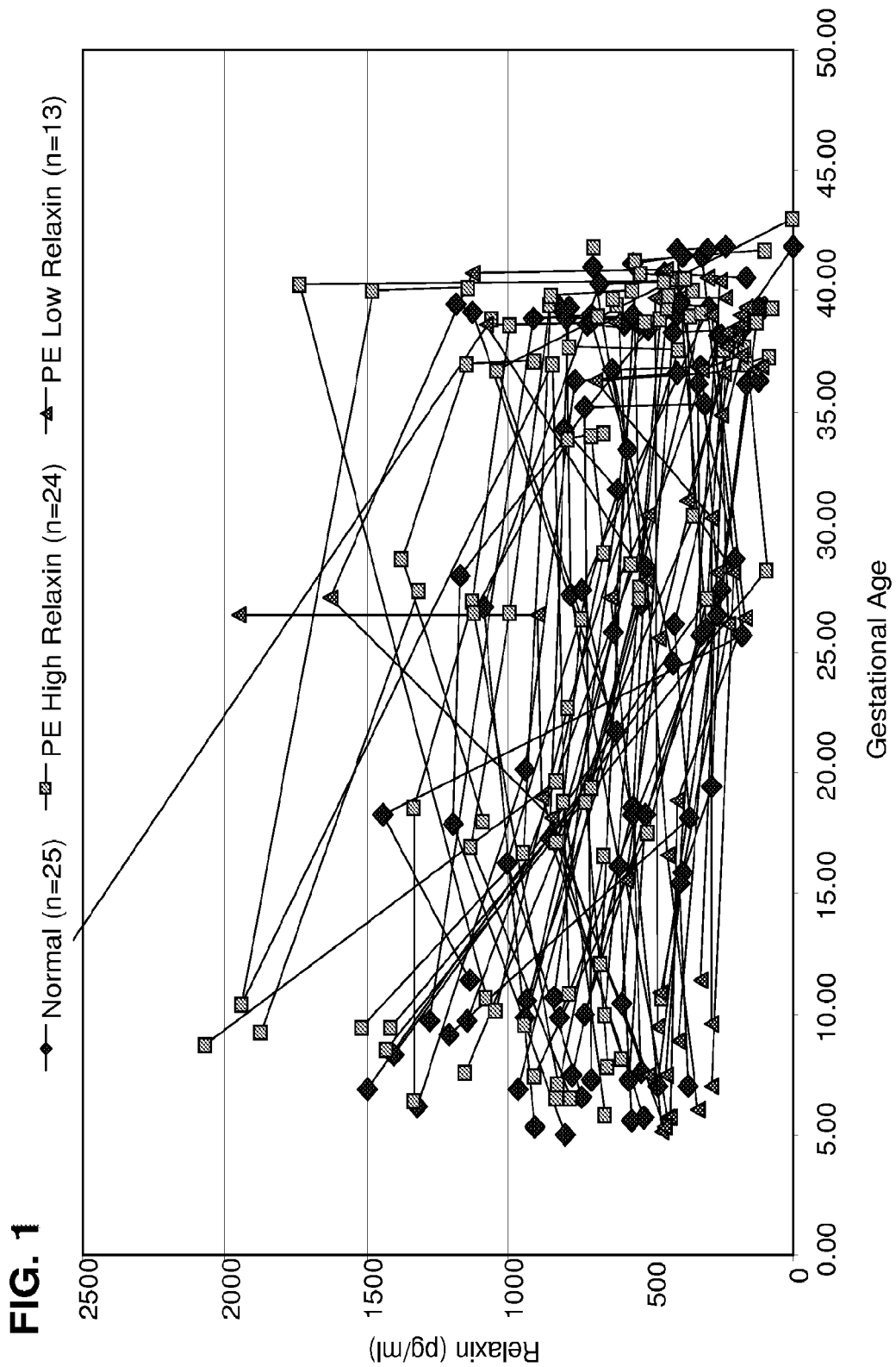
FIG. 1 depicts serum relaxin concentrations in preeclamptic (PE) women (HPU and HP groups) with respect to gestational age. The lines connect samples from the same subject. The triangles depict samples from pregnant women who later developed preeclampsia and had endogenous relaxin levels below 500 pg/ml in the first 15 weeks. The squares depict samples from pregnant women who later developed preeclampsia but who had endogenous relaxin levels above about 500 pg/ml. The diamonds depict samples from pregnant women who did not develop preeclampsia. It should be noted that few of the women having normal pregnancy outcomes had relaxin concentrations in the first 15 weeks that were below 500 pg/ml.
Figure 2:
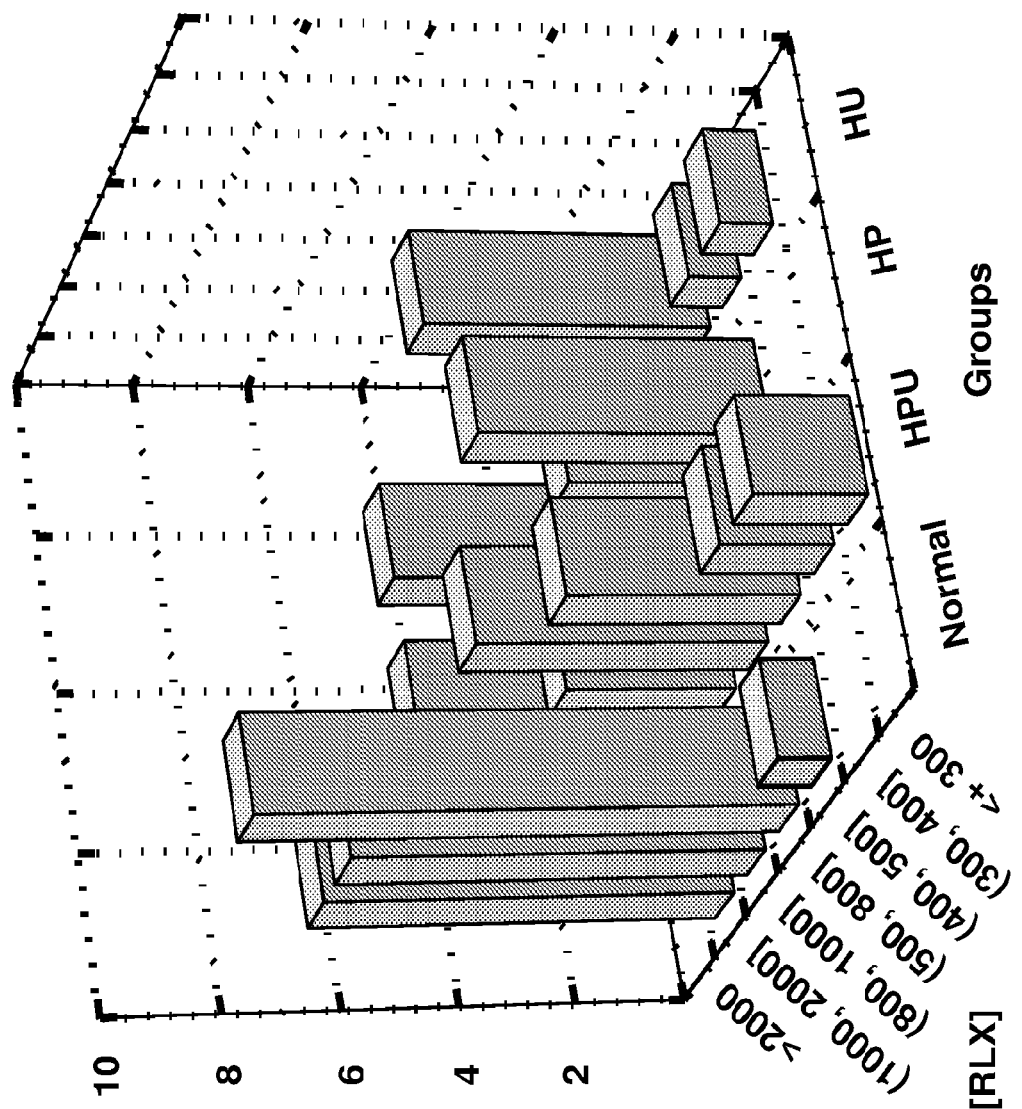
FIG. 2 is an illustration of a bivariate histogram (i.e., preeclampsia cluster) of the relaxin concentration of the first sample collected from study subjects. The first sample was obtained from 5 to 11 weeks of gestational age, as subjects were recruited into the study at different times.
Figure 3:
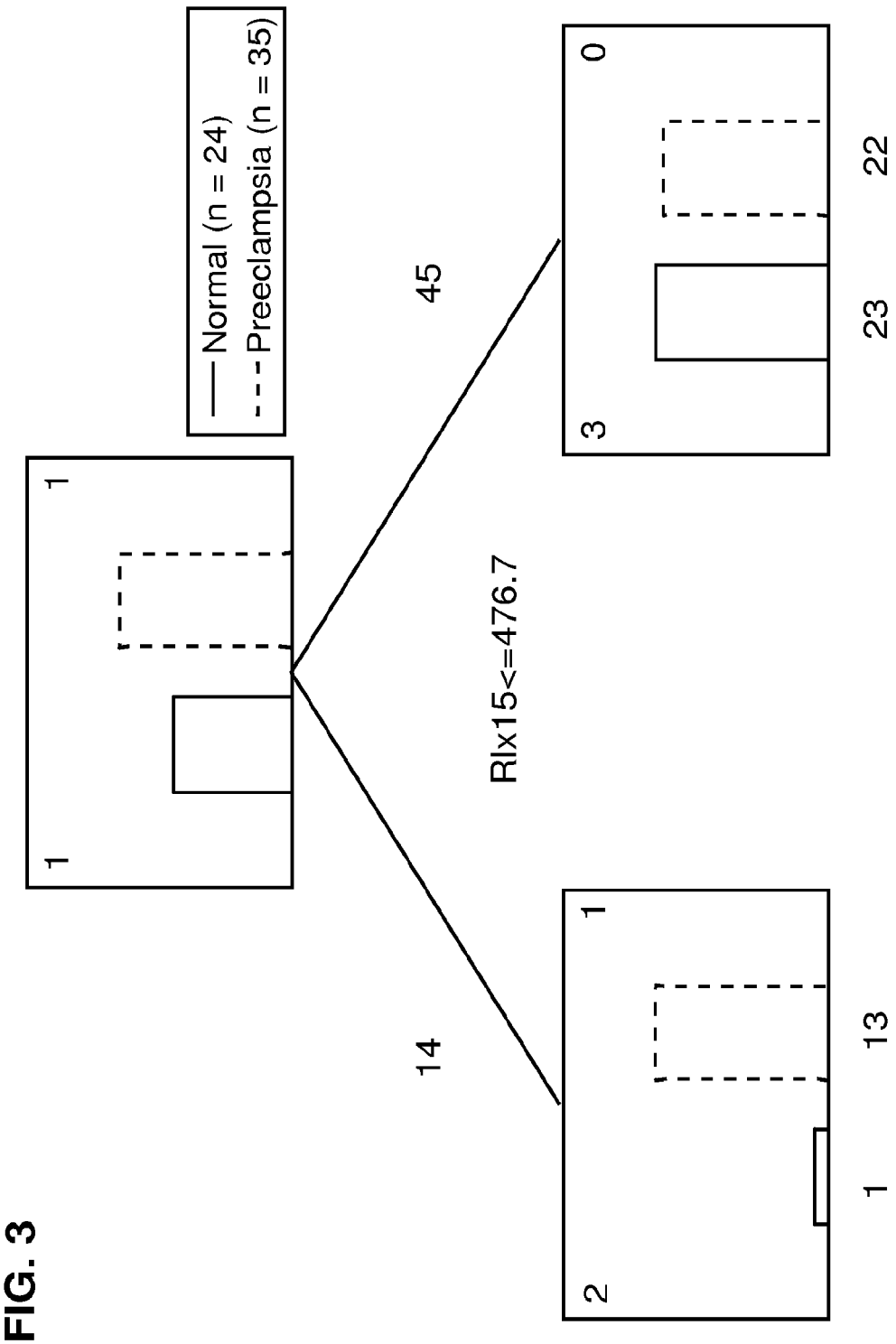
FIG. 3 is an illustration of a classification and regression tree (CART) for HPU and HP gestations (i.e., preeclamptic women), in which the number of splits is one and the number of terminal nodes is two. The specificity with relaxin (Rlx) is 96% while the sensitivity is 37%. The data used for this classification tree is shown in FIG. 1. This illustrates that serum relaxin can be used to identify a population of women that have a high risk of developing preeclampsia later in their pregnancy. This prediction can be made months in advance of the appearance of clinical symptoms of preeclampsia.
Figure 4:
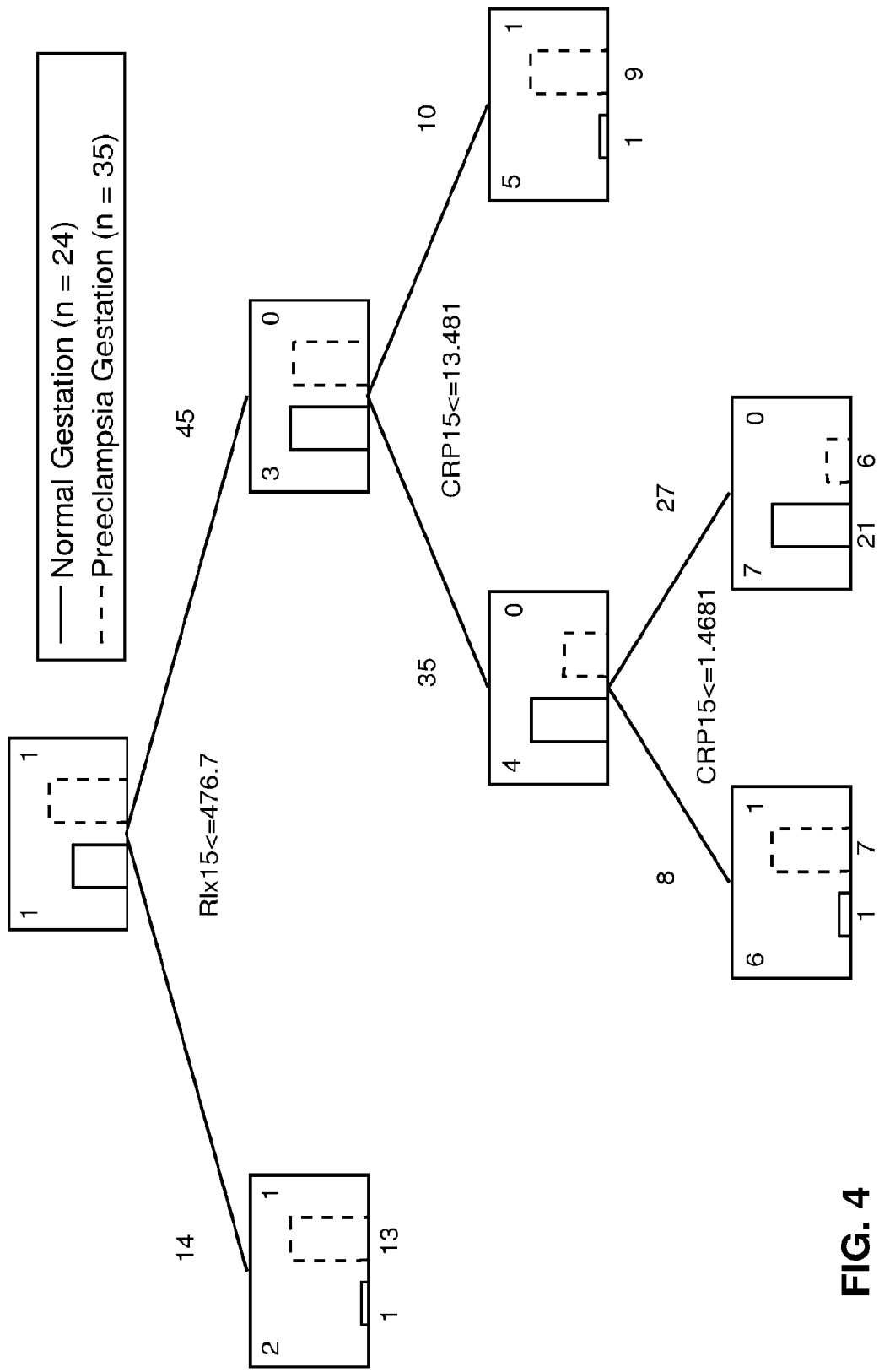
FIG. 4 shows a CART analysis for HPU and HP gestations (i.e., preeclamptic women), in which the number of splits is three and the number of terminal nodes is four. With relaxin (Rlx) and C-reactive protein (CRP) the specificity is 93% while the sensitivity improved to 83% compared to relaxin (Rlx) alone (see FIG. 3). The addition of a CRP measurement makes it possible to identify women predisposed to preeclampsia that were not identified by determination of relaxin (Rlx) concentration alone.

As described herein, measuring relaxin levels in pregnant women can predict if the women will develop preeclampsia. As such, low levels of relaxin are a highly specific indicator of the condition. The term relaxin (natural relaxin and endogenous relaxin) as used herein in reference to human subjects refers to H2 relaxin, unless otherwise specified. FIGS. 1 and 3 illustrate that when relaxin levels in pregnant women are below 500 pg/ml, the likelihood that the women will develop preeclampsia is as high as 96 percent (see FIG. 3 for CART analysis). In fact, one third of the preeclamptic women identified using the data in FIG. 1 have relaxin levels below 500 pg/ml. In further embodiments, by measuring natural C-reactive protein (CRP) levels in addition to relaxin levels, the test becomes even more sensitive. For example FIG. 4 illustrates that when CRP is less then about 1.5 µg/ml or more than about 13.5 µg/ml, the sensitivity of the test increased to 83 percent.

In another aspect, the disclosure provides methods of preventing or reducing the likelihood of the development of preeclampsia through administration of pharmaceutically active H2 relaxin or a H2 relaxin agonist. More specifically, exogenous H2 relaxin can be administered to pregnant women if endogenous relaxin levels are below 500 pg/ml in order to stabilize the women during pregnancy and prevent preeclampsia from developing. As such, the pregnant women are treated with a pharmaceutical formulation of synthetic or recombinant human relaxin or relaxin agonist throughout the terminal part of gestation (e.g., subsequent to H2 measurement), wherein relaxin functions primarily as prophylactic agent.

DEFINITIONS

The terms "endogenous relaxin" or "natural relaxin" are used interchangeably herein and refer to the naturally occurring peptide hormone relaxin which is well known in the art. In women, relaxin is produced by the corpus luteum of the ovary, the breast and, during pregnancy, also by the placenta, chorion, and decidua. Endogenous relaxin levels rise after ovulation as a result of its production by the corpus luteum and peak in the mid and late luteal phase of the menstrual cycle. If the cycle in nonconceptive, relaxin concentrations decline to undetectable. However, if the cycle is conceptive, relaxin concentrations rapidly increase and peak in the first trimester. Relaxin concentrations then begin a slow decline but remain elevated throughout gestation. The term relaxin (natural relaxin and endogenous relaxin) as used herein in reference to human subjects refers to H2 relaxin, unless otherwise specified.

The term "exogenous relaxin", as used herein, means non-endogenous human relaxin, including intact full length human relaxin or a portion of the relaxin molecule that retains biological activity. The term "exogenous relaxin" encompasses human H1 preprorelaxin, prorelaxin, and relaxin; H2 preprorelaxin, prorelaxin, and relaxin; and H3 preprorelaxin, prorelaxin, and relaxin. The term "relaxin" further includes biologically active (also referred to herein as "pharmaceutically active") relaxin from recombinant, synthetic or native sources as well as relaxin variants, such as amino acid sequence variants. As such, the term encompasses synthetic human relaxin and recombinant human relaxin, including synthetic H1, H2 and H3 human relaxin and recombinant H1, H2 and H3 human relaxin. The term further encompasses active agents with relaxin-like activity, such as relaxin agonists, relaxin mimetics and/or relaxin analogs and portions thereof that retain biological activity, including all agents that competitively displace bound relaxin from a relaxin receptor (e.g., LGR7 receptor, LGR8 receptor, GPCR135, GPCR142, etc.). Thus, a pharmaceutically effective relaxin agonist or mimetic is any agent with relaxin-like activity that is capable of binding to a relaxin receptor to elicit a relaxin-like response. In addition, the nucleic acid sequence of human relaxin as used herein does not necessarily have to be 100% identical to nucleic acid sequence of human relaxin (e.g., H1, H2 and/or H3) but may be at least about 40%, 50%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the nucleic acid sequence of human relaxin. Relaxin, as used herein, can be made by any method known to those skilled in the art. Examples of such methods are illustrated, for example, in U.S. Pat. No. 5,759,807 as well as in Büllesbach et al. (1991) *The Journal of Biological Chemistry* 266(17):10754-10761. Examples of relaxin molecules and analogs are illustrated, for example, in U.S. Pat. No. 5,166,191.

Naturally occurring biologically active relaxin may be derived from human, murine (i.e., rat or mouse), porcine, or other mammalian sources. Also encompassed is relaxin modified to increase in vivo half life, e.g., PEGylated relaxin (i.e., relaxin conjugated to a polyethylene glycol), modifications of amino acids in relaxin that are subject to cleavage by degrading enzymes, and the like. The term also encompasses relaxin comprising A and B chains having N- and/or C-terminal truncations. In general, in H2 relaxin, the A chain can be varied from A(1-24) to A(10-24) and the B chain from B(1-33) to B(10-22); and in H1 relaxin, the A chain can be varied from A(1-24) to A(10-24) and the B chain from B(1-32) to B(10-22). Also included within the scope of the term "relaxin" are other insertions, substitutions, or deletions of one or more amino acid residues, glycosylation variants, unglycosylated relaxin, organic and inorganic salts, covalently modified derivatives of relaxin, preprorelaxin, and prorelaxin. Also encompassed in the term is a relaxin analog having an amino acid sequence which differs from a wild-type (e.g., naturally-occurring) sequence, including, but not limited to, relaxin analogs disclosed in U.S. Pat. No. 5,811,395. Possible modifications to relaxin amino acid residues include the acetylation, formylation or similar protection of free amino groups, including the N-terminal, amidation of C-terminal groups, or the formation of esters of hydroxyl or carboxylic groups, e.g., modification of the tryptophan (Trp) residue at B2 by addition of a formyl group. The formyl group is a typical example of a readily-removable protecting group. Other possible modifications include replacement of one or more of the natural amino-acids in the B and/or A chains with a different amino acid (including the D-form of a natural amino-acid), including, but not limited to, replacement of the Met moiety at B24 with norleucine (Nle), valine (Val), alanine (Ala), glycine (Gly), serine (Ser), or homoserine (HomoSer). Other possible modifications include the deletion of a natural amino acid from the chain or the addition of one or more extra amino acids to the chain. Additional modifications include amino acid substitutions at the B/C and C/A junctions of prorelaxin, which modifications facilitate cleavage of the C chain from prorelaxin; and variant relaxin comprising a non-naturally occurring C peptide, e.g., as described in U.S. Pat. No. 5,759,807.

Also encompassed by the term "relaxin" are fusion polypeptides comprising relaxin and a heterologous polypeptide. A heterologous polypeptide (e.g., a non-relaxin polypeptide) fusion partner may be C-terminal or N-terminal to the relaxin portion of the fusion protein. Heterologous polypeptides include immunologically detectable polypeptides (e.g., "epitope tags"); polypeptides capable of generating a detectable signal (e.g., green fluorescent protein, enzymes such as alkaline phosphatase, and others known in the art); therapeutic polypeptides, including, but not limited to, cytokines, chemokines, and growth factors. All such variations or alterations in the structure of the relaxin molecule resulting in variants are included within the scope of this disclosure so long as the functional (biological) activity of the relaxin is maintained. Preferably, any modification of relaxin amino acid sequence or structure is one that does not increase its immunogenicity in the individual being treated with the relaxin variant. Those variants of relaxin having the described functional activity can be readily identified using in vitro and in vivo assays known in the art.

In some embodiments, the present disclosure provides methods comprising administration of a relaxin agonist. In some methods, the relaxin agonist activates one or more relaxin-related G-protein coupled receptors (GPCR) selected from but not limited to RXFP1, RXFP2, RXFP3, RXFP4, FSHR (LGR1), LHCGR (LGR2), TSHR (LGR3), LGR4, LGR5, LGR6LGR7 (RXFP1) and LGR8 (RXFP2). In some embodiments, the relaxin agonist comprises the amino acid sequence of Formula I of WO 2009/007848 of Compugen (herein incorporated by reference for the teaching of relaxin agonist sequences). Exemplary relaxin agonists are also disclosed in international application PCT/US2009/044251 of Corthera, which is hereby incorporated by reference for the teaching of relaxin agonist sequences of SEQ ID NOS:4-8.

The present disclosure also encompasses homologues of Formula I polypeptides, such homologues can be at least 50%, at least 55%, at least 60%, at least 65%, at least 70%, at least 75%, at least 80%, at least 85%, at least 85%, at least 90%, at least 95% or more say 100% identical to the amino acid sequence of an exemplary relaxin agonist (e.g., SEQ ID NO:5 or SEQ ID NO:6 of PCT/US2009/044251 of Corthera), as can be determined using BlastP software of the National Center of Biotechnology Information (NCBI) using default parameters, optionally and preferably including the following: filtering on (this option filters repetitive or low-complexity sequences from the query using the Seg (protein) program), scoring matrix is BLOSUM62 for proteins, word size is 3, E value is 10, gap costs are 1 l, 1 (initialization and (initialization and extension). Optionally and preferably, nucleic acid sequence identity/homology is determined with BlastN software of the National Center of Biotechnology Information (NCBI) using default parameters, which preferably include using the DUST filter program, and also preferably include having an E value of 10, filtering low complexity sequences and a word size of 11. Finally the present disclosure also encompasses fragments of the above described polypeptides and polypeptides having mutations, such as deletions, insertions or substitutions of one or more amino acids, either naturally occurring or artificially induced, either randomly or in a targeted fashion.

The term "pregnancy" refers to the nine months (40 weeks from the last menstrual period) of pregnancy which is traditionally divided into three trimesters, i.e., distinct periods of roughly three months in which different phases of fetal development take place. The first trimester is a time of basic cell differentiation. It is believed to end at the mother's first perception of fetal movement (quickening), which usually occurs around the end of the third month (or about 12 to about 14 weeks of gestational age). The second trimester is a period of rapid growth and maturation of body systems (about 15 to about 28 weeks of gestational age). A second-trimester fetus born prematurely may be viable, depending on the hospital care. The third trimester marks the final stage of fetal growth, in which systems are completed, fat accumulates under the fetus' skin, and the fetus moves into position for birth (about 29 to about 42 weeks of gestational age). This trimester ends with the birth itself.

The term "about" when used in the context of a stated value, encompasses a range of up to 10% above or below the stated value (e.g., 90-110% of the stated value). For instance, an intravenous (IV) infusion rate of about 30 mcg/kg/day, encompasses IV infusion rates of 27 mcg/kg/day to 33 mcg/kg/day.

"Therapeutically effective" refers to the amount of pharmaceutically active relaxin that will result in a measurable desired medical or clinical benefit to a patient, as compared to the patient's baseline status or to the status of an untreated or placebo-treated (e.g., not treated with relaxin) subject.

Preeclampsia

Preeclampsia (or pre-eclampsia) can be caused by a shallowly implanted placenta that becomes hypoxic, leading to an immune reaction characterized by secretion of up-regulated inflammatory mediators from the placenta that act upon the vascular endothelium. Shallow implantation may stem from the maternal immune system's response to the placenta. This theory refers to evidence suggesting a lack of established immunological tolerance to paternal antigens from the fetus and its placenta. In some cases of preeclampsia it is thought that the mother lacks the receptors for the proteins the placenta secretes to down-regulate the maternal immune response (Moffett et al., Placenta Suppl. A:S51-6, 2007). However, in many cases of preeclampsia, the maternal response to the placenta appears to have allowed normal implantation to take place. It is possible that women with higher baseline levels of inflammation stemming from underlying conditions such as chronic hypertension or autoimmune disease may have less tolerance for the inflammatory impact of pregnancy.

Many theories have attempted to explain why preeclampsia arises, and have linked the syndrome to the presence of the following conditions, including, endothelial cell injury, immune rejection of the placenta, compromised placental perfusion, altered vascular reactivity, imbalance between prostacyclin and thromboxane, decreased glomerular filtration rate with retention of salt and water, decreased intravascular volume, increased central nervous system irritability, disseminated intravascular coagulation, uterine muscle stretch (ischemia), dietary factors, including vitamin deficiency, and genetic factors.

The understanding of preeclampsia is as a two-stage process, with a highly variable first stage which predisposes the placenta to hypoxia, followed by the release of soluble factors that result in, for example, endothelial cell injury, altered vascular reactivity, the classic lesion of glomerular endotheliosis, decreased intravascular volume, inflammation, and the like. Some studies support the notion of an inadequate blood supply to the placenta resulting in the release of hormones or chemical agents that, in mothers predisposed to the condition, cause damage to the endothelium (lining of blood vessels), alterations in metabolism, inflammation, and other pathological reactions (Drife and Magowan (eds). *Clinical Obstetrics and Gynaecology*, Chapter 39, pages 367-370).

Some studies suggest that hypoxia resulting from inadequate perfusion up-regulates sFlt-1, a VEGF and PLGF antagonist, leading to damage of maternal endothelium and restriction of placental growth (Maynard et al., *J Clin Invest*, 111(5):649-58, 2003). In addition, endoglin, a TGF-beta antagonist, is elevated in pregnant women who develop preeclampsia (Venkatesha et al., *Nat Med*, 12(6):642-649, 2006). Soluble endoglin is likely up-regulated by the placenta in response to an up-regulation of cell-surface endoglin produced by the maternal immune system, although there is also the potential that sEng is produced by the maternal endothelium. Levels of both sFlt-1 and sEng increase as severity of disease increases, with levels of sEng exceeding levels of sFlt-1 in HELLP syndrome cases. The HELLP syndrome is a severe variant of preeclampsia that features hemolysis, elevated liver enzymes, and low platelets. Both sFlt-1 and sEng are up-regulated in all pregnant women to some extent, supporting the idea that hypertensive disease in pregnancy is a normal pregnancy adaptation gone awry. Initial maternal rejection of the placental cytotrophoblasts may be the cause of the inadequately remodeled spiral arteries in those cases of preeclampsia associated with shallow implantation, leading to downstream hypoxia and the appearance of maternal symptoms in response to up-regulated sFlt-1 and sEng.

It has also been documented that fetal cells such as fetal erythroblasts, as well as cell-free fetal DNA are increased in the maternal circulation in women who develop preeclampsia. These findings have given rise to the hypothesis that preeclampsia is a disease process by which a placental lesion such as a hypoxic lesion allows increased fetal material to enter into the maternal circulation leading to an immune response and endothelial damage ultimately resulting in preeclampsia and eclampsia.

Statistics show that preeclampsia and related pregnancy disorders, such as eclampsia and hypertensive disorders of pregnancy, are responsible for the majority of maternal deaths, as well as death and illness among infants, worldwide. Approximately 76,000 women die annually due to these disorders. Preeclampsia is especially dangerous because some women experience no symptoms at all. This is why improved screening and prediction is imperative for diagnosing this condition. After women are diagnosed with preeclampsia or hypertensive gestation they may receive any one or more of the following medications including methyldopa, hydralazine, labetalol, nifedipine, magnesium sulfate, betamethasone and dexamethasone.

Preventative strategies such as calcium, aspirin and antioxidants (e.g., vitamins C and E) have not been fully successful. In some cases, there may be a small reduction in the risk of preeclampsia with aspirin based on meta-analysis (PARIS collaboration), but it is not a cure. Tight control of blood pressure may prevent serious maternal morbidity such as stroke, but also does not fully treat the disease.

Relaxin

Endogenous or natural relaxin is a peptide hormone that is similar in size and shape to insulin. More specifically, relaxin is an endocrine and autocrine/paracrine hormone that belongs to the insulin gene superfamily. The active form of the encoded protein consists of an A chain and a B chain, held together by disulphide bonds, two inter-chains and one intra-chain. Thus, the structure closely resembles insulin in the disposition of disulphide bonds. In humans, there are three known non-allelic relaxin genes, relaxin-1 (RLN-1 or H1), relaxin-2 (RLN-2 or H2) and relaxin-3 (RLN-3 or H3). H1 and H2 share high sequence homology. There are two alternatively spliced transcript variants encoding different isoforms described for this gene. H1 and H2 are differentially expressed in reproductive organs (see U.S. Pat. No. 5,023,321; and Garibay-Tupas et al., *Molecular and Cellular Endocrinology* 219:115-125, 2004), while H3 is found primarily in the brain. The evolution of the relaxin peptide family and its receptors is described in the art (see Wilkinson et al., *BMC Evolutionary Biology* 5(14):1-17, 2005; and Wilkinson and Bathgate, Chapter 1, Relaxin and Related Peptides, Landes Bioscience and Springer Science+Business Media, 2007).

Relaxin is believed to activate specific relaxin receptors, i.e., LGR7 (RXFP1) and LGR8 (RXFP2) as well as GPCR135 and GPCR142. LGR7 and LGR8 are leucine-rich repeat-containing, G protein-coupled receptors (LGRs), which represent a unique subgroup of G protein-coupled receptors. They contain a heptahelical transmembrane domain and a large glycosylated ectodomain, distantly related to the receptors for the glycoproteohormones, such as the LH-receptor or FSH-receptor. These relaxin receptors are found in the heart, smooth muscle, connective tissue, and central and autonomous nervous system. Potent relaxins such as H1, H2, porcine and whale relaxin possess a certain sequence in common. Relaxins that deviate from the conserved H1 and H2 sequence, such as rat, shark, dog and horse relaxins show a reduction in bioactivity through the LGR7 and LGR8 receptors (Bathgate et al., *Ann NY Acad Sci*, 1041: 61-76, 2005; Receptors for Relaxin Family Peptides). However, similar to H2 relaxin, H3 relaxin activates the LGR7 receptor (Satoko et al., *J Biol Chem*, 278(10):7855-7862, 2003). In addition, H3 has been shown to activate the GPCR135 receptor (Van der Westhuizen, *Ann NY Acad Sci,* 1041:332-337, 2005) and GPCR142 receptor. GPCR135 and GPCR142 are two structurally related G-protein-coupled receptors. Mouse and rat GPCR135 exhibit high homology (i.e., greater than 85%) to the human GPCR135 and have very similar pharmacological properties to that of the human GPCR135. Human and mouse as well as rat relaxin-3 binds to and activates mouse, rat, and human GPCR135 at high affinity. In contrast, the mouse GPCR142 is less well conserved (i.e., 74% homology) with human GPCR142. GPCR142 genes from monkey, cow, and pig were cloned and shown to be highly homologous (i.e., greater than 84%) to human GPCR142. Pharmacological characterization of GPCR142 from different species has shown that relaxin-3 binds to GPCR142 from different species at high affinity (Chen et al., *Journal of Pharmacology and Experimental Therapeutics,* 312(1):83-95, 2005).

Relaxin and Pregnancy

The characteristic function of relaxin is associated with the female reproductive tract physiology, which includes the regulation of biochemical processes involved in remodeling the extracellular matrix of the cervix and vagina during pregnancy and rupture of the fetal membranes at term. These modifications enable the offspring to move through the birth canal and prevent dystocia (i.e., significant slowing or cessation of the fetus's descent or the cervix's dilatation or both during delivery). In addition, relaxin promotes uterine and placental growth and influences vascular development and proliferation in the endometrium (Parry et al., *Adv Exp Med Biol,* 612:34-48, 2007).

In humans, relaxin found in circulation is produced mainly by the corpus luteum of the ovary, in both pregnant and non-pregnant females. It rises to a peak within approximately 14 days of ovulation and then declines in the absence of pregnancy resulting in menstruation. During the first trimester of pregnancy serum levels rise. In addition, relaxin is produced by the decidua and trophoblast but this relaxin is not thought to enter the circulation. The peak of relaxin is reached during the 14 weeks of the first trimester. Relaxin is notable for the growth and remodeling of reproductive and several other tissues during pregnancy. As noted above, the action of relaxin is mediated via relaxin receptors.

Children who are born to preeclamptic mothers often have low birth weight and are at greater risk for subsequent cardiovascular conditions later in life. Mothers who deliver babies with low birth weights are at greater risk for ischemic heart disease and death. Specifically, preeclamptic women who deliver a small infant early, have a rate of hospital admission for ischemic heart disease or death that is ten times higher than control women. There is very strong evidence that cardiovascular risk is increased in women with preeclampsia compared to women who do not suffer from this condition. In fact, any hypertensive disorder of pregnancy increases later risk for hypertension and stroke. It is also known that two to four months after delivery, two thirds of preeclamptic women may still have microalbuminuria (i.e., leakage of small amounts of protein, e.g., albumin, into the urine). In postmenopausal women, microalbuminuria is a substantial cardiovascular risk factor. In addition, preeclampsia is associated with insulin resistance and elevated homocysteine levels, which represent a long-term risk in women (Davison et al., *J Am Soc Nephrol,* 15:2440-2448, 2004).

During normal pregnancy, glomerular filtration rate (GFR) and renal plasma flow increase by 40 to 65 and 50 to 85 percent, respectively. Notably, relaxin mediates renal vasodilation during pregnancy. Relaxin is known to increase vascular gelatinase activity, thereby converting big ET to $ET_{1-32}$, which leads to renal vasodilation, hyperfiltration and reduced myogenic reactivity of small renal arteries via the endothelial $ET_B$ receptor and nitric oxide (Jeyabalan et al., *Frontiers in Bioscience* 12:2425-2437, 2007).

Uric acid is the end product of purine metabolism. Purines are naturally produced by the body and are also derived from the diet. In humans, most circulating uric acid is produced by the liver and about 66 percent is excreted by the kidney, while about 33 percent is excreted by the gastrointestinal tract. The serum concentration of uric acid usually falls during normal pregnancy as a consequence of increased GFR, reduced proximal tubular reabsorption, and possible alteration in the electrostatic charge of the glomerular filter. It is believed that anti-angiogenic factors that come from the placenta in preeclampsia could contribute to glomerular endotheliosis (i.e., the renal histologic lesions characteristic of preeclampsia), proteinuria, and hypertension during the disease. In most women with preeclampsia, renal plasma flow and glomerular filtration rate are slightly decreased as a consequence of increased afferent arteriolar resistance and/or reduced ultrafiltration coefficient. This serum uric acid concentration is primarily increased because of reduced renal clearance. Reduced GFR leads to a decreased filtered load of uric acid. In addition, plasma volume contraction contributes to increased proximal tubular reabsorption coupled to sodium. The increase in urinary protein excretion in preeclampsia occurs secondary to alterations in the size and/or charge selectivity of the glomerular filter, possible increases in glomerular capillary pressure, and compromise of proximal tubular reabsorption (see Jeyabalan et al., supra).

During a normal human pregnancy, the urinary excretion of total protein, albumin, low molecular weight proteins, and renal tubular enzyme increases. In preeclamptic pregnancy, renal function is reduced. According to some studies, GFR and effective renal plasma flow (ERPF) are reduced by 32 percent and 24 percent, respectively (see Jeyabalan et al., supra). The precise mechanism responsible for the compromise in renal circulation in preeclampsia is still unknown. The reduced ERPF is believed to be due to high renal vascular resistance. An elevated renal afferent (pre-glomerular aerteriolar) resistance may be the major contributor to the increased total renal vascular resistance. Herein, the increased afferent arteriolar tone in preeclampsia may protect the glomerulus from damage due to high systemic arterial pressures. The reduced ERPF, the ultrafiltration coefficient, or both could be possible mechanisms for the reduced GFR in preeclampsia (see Jeyabalan et al., supra).

Without wanting to be bound by theory, the underlying mechanism of action of relaxin is widely thought to be based on stimulating vasodilation and angiogenesis. First, relaxin is believed to stimulate angiogenesis in the uterus to provide a better connection of the fetal and maternal blood vessels (i.e., to increase the number of maternal spiral arteries, to modify maternal spiral arteries and/or promote trophoblast invasion of maternal spiral arteries). Increasing angiogenesis and vasodilation targets the pathogenesis of preeclampsia, namely an insufficient blood supply from mother to child and reduced placental and maternal organ perfusion. When relaxin is administered to pregnant women, relaxin binds to receptors in the uterus and placenta and stimulates VEGF production. VEGF, in turn, binds to endothelial cells to stimulate angiogenesis. This provides for a better blood supply between mother and child. Second, relaxin is a potent vasodilator and thus may improve uteroplacental and maternal systemic organ perfusion, both of which are reduced in women with preeclampsia. Relaxin works through the nitric oxide synthase pathway, thereby stimulating nitric oxide NO to increase vasodilation in humans. Thus, administration of relaxin during pregnancy may prevent the development of one of the most detrimental symptoms of preeclampsia (i.e., high blood pressure at or above levels of 140/90 mmHg). Third, glomerular filtration rate (GFR) and renal plasma flow (RPF) are known to decrease in preeclampsia which is a serious hypertensive complication of pregnancy. Thus administration of relaxin may also increase renal blood flow in pregnant women, thereby further reducing the risks of preeclampsia. In addition, relaxin has potential anti-inflammatory effects.

C-Reactive Protein (CRP) and Pregnancy

CRP refers to a plasma protein that is produced by the liver in response to inflammation in the body. The inflammation may be caused by an injury, an infection or a condition such as high blood pressure. CRP is considered to be part of the innate immune system and a marker of chronic systemic inflammation. CRP is also an independent predictor of cardiovascular events. It is believed that CRP is increased in normal pregnancy as an acute phase reactant, just as albumin synthesis is decreased due to IL-6 and other cytokines that increase in the circulation. Notably, IL-1 and IL-6 levels are higher in preeclampsia, which may explain why CRP levels are also higher in preeclampsia. This finding is consistent with the inflammatory response of normal pregnancy, which is exaggerated during preeclampsia. Thus, testing pregnant women for serum CRP levels in addition to serum relaxin levels can provide additional insight into how likely these women are to develop preeclampsia. By using CRP as another factor, the sensitivity of the H2 relaxin test described herein is increased.

Serum CRP has also been found to be elevated in women with a history of eclampsia (e.g., seizures during preeclamptic pregnancy). In fact, women with a history of preeclampsia or eclampsia are at an increased risk for cardiovascular disease after pregnancy for reason(s) that remain unclear. It is believed that inflammation, dyslipidemia and insulin resistance are associated with a higher risk of preeclampsia, and CRP, when elevated, is an indicator of inflammation and cardiovascular risk (Hubel et al., *Hypertension* 51:1499-1505, 2008).

Low Relaxin Levels Predict Preeclampsia

CART (classification and regression tree) was used to analyze the data obtained from pregnant women during the study disclosed in the experimental examples. The parameters used for preeclampsia prediction were relaxin and, optionally, C-reactive protein (CRP). As can be seen in FIG. 1, the gestational age during pregnancy was broken down into three periods, i.e., 0-15 weeks (first trimester), 15-25 weeks (second trimester), and 25-35 weeks (third trimester). It is beneficial to test pregnant women as early as possible for markers of preeclampsia in order to begin treatments to prevent the disease from fully developing. Thus, testing women in the first trimester is preferable to testing women during the second or third trimester of pregnancy. It may be possible to test women in the second and/or third trimester of pregnancy if testing was not possible earlier.

CART is a non-parametric technique that produces either a classification or regression tree, depending on whether the dependent variable is categorical or numeric, respectively. The trees are formed by a collection of rules based on values of certain variables in the modeling data set. As such, the rules are selected based on how well splits based on variables' values can differentiate observations based on the dependent variable. Once a rule is selected and splits a node into two, the same logic is applied to each child node (i.e., it is a recursive procedure). Splitting stops can be made when CART detects no further gain, or some preset stopping rules are met. Each branch of the tree ends in a terminal node. Each observation falls into one and exactly one terminal node and each terminal node is uniquely defined by a set of rules.

Preeclampsia is generally defined by symptoms such as hypertension and proteinuria. Some pregnant women also suffer from elevated uric acid. Thus, preeclamptic women fall into two groups, those that exhibit hypertension and proteinuria (HP) and those that exhibit hypertension, proteinuria and uric acid (HPU). Notably, when pregnant women do not exhibit symptoms of proteinuria they are usually considered to have a hypertensive pregnancy rather than preeclampsia, such as when they exhibit hypertension and elevated uric acid (HU). For the purpose of CART analysis discussed herein, the following groups are defined in Table 1.

TABLE 1

| |
|---|
| Normal Gestation |
| HPU = hypertension, proteinuria, uric acid |
| HP = hypertension, proteinuria |
| HU = hypertension, uric acid |
| Preeclampsia = HPU and HP combined |
| Hypertensive Pregnancy = HPU, HP and HU combined |

Referring to the classification tree of FIG. 3, the number of splits is one and the number of terminal nodes is two. More specifically, the top box shows that there are 35 subjects classified as preeclamptic (dashed line), and 24 subjects classified as normal (solid line). Of the 59 total study subjects, 14 subjects had a H2 relaxin level below 476.7 pg/ml and 45 subjects had a H2 relaxin level above 476.7 pg/ml. In order to further determine how specific the relaxin test is, the preeclamptic and normal subjects are split into two groups, one box on the left shows those below 476.7 pg/ml relaxin and one box on the right shows those above 476.7 pg/ml relaxin. As can be seen on the left, out of those with relaxin levels below 476.7 pg/ml relaxin, 13 individuals developed preeclampsia, while only one individual had a normal pregnancy making this test highly specific (see Example 2 for a more detailed analysis).

A separate smaller study was conducted using samples obtained from a less well-defined population of pregnant women from Australia. In the second study, only two samples contained less than 500 pg/ml relaxin, and of these two only one sample was obtained from a preeclamptic subject. This differs from the first larger study conducted using samples taken at defined gestational ages from pregnant women from North America (e.g., Pittsburgh, Pa.). In addition to suspected sampling differences between the two studies, the Australian study population is presumed to be a homogenous Caucasian population, whereas over 30% of the subjects of the North American study population were African American. Accordingly, in preferred embodiments blood samples are obtained from pregnant women during the first trimester of pregnancy. In some embodiments, the pregnant women are North American. In a subset of these embodiments, the North American subjects are from the United States and/or Canada. In further embodiments, the study subjects are of African descent.

Administration of Relaxin Prevents Development of Preeclampsia

Preeclampsia is a dangerous condition and can appear at any time during the pregnancy, delivery and up to six weeks post-partum, though it most frequently occurs in the final trimester and most often not until weeks 20-35 of gestation. Preeclampsia can develop gradually, or come on quite suddenly, even flaring up in a matter of hours, though the signs and symptoms may not have been noticed for months. When preeclampsia is silent, showing up unexpectedly during a routine blood pressure check and/or urine test and the baby is near term (after 36 weeks), then labor is induced, the baby is delivered and the mother is carefully monitored. If preeclampsia occurs earlier in the pregnancy, its impact is even more profound. For instance, bed rest, medication and even hospitalization may be prescribed to keep the mother's blood pressure under control. It is in the best interest of the baby to be kept in-utero as long as possible. Unfortunately, the only cure for preeclampsia is delivery of the baby, and it may be in the best interest of the mother to delivery the baby before term. The physician may prescribe anti-hypertensive medications, such as beta-blockers, calcium channel blockers, hydralazine, alpha-methyldopa, clonidine, and in rare cases, lasix or diuretics (water pills), though the latter is generally not advisable. If the blood pressure cannot be managed with medication and treatment and the mother's and/or infant's health is at risk, then the mother may be given steroids to aid the maturation of the infant's lungs so that a viable baby can be delivered prematurely.

The present disclosure provides a method of identifying pregnant woman predisposed to preeclampsia so that steps can be taken to reduce the likelihood that she will develop preeclampsia. The present disclosure further provides methods of reducing risk of or preventing preeclampsia by administering H2 relaxin to a pregnant woman in the first and/or second trimester of pregnancy when a level of H2 relaxin of less then about 500 pg/ml is measured in plasma or serum from a blood sample obtained during her first trimester of pregnancy. H2 relaxin is preferably prophylactically administered to pregnant women as soon as low relaxin levels (e.g., below 500 pg/ml) are detected. However, preeclampsia does often not manifest until weeks 20-35 of gestation. Thus, if relaxin is administered later during pregnancy prior to manifestation of symptoms, it may still be beneficial in reducing the likelihood of full blown preeclampsia.

In one embodiment of the disclosure, relaxin is synthetic human relaxin. In another embodiment of the disclosure, relaxin is a recombinant human relaxin. In yet another embodiment of the disclosure, relaxin is a relaxin agonist or relaxin mimetic. If relaxin is administered, it is preferably H2 relaxin. In further embodiments, the relaxin is a chimeric relaxin comprising an A or a B chain of H2 relaxin and an A or a B chain of H1 or H2 relaxin, Synthetic human relaxins and chimeras are available from CBL Biopharma (Boulder, Colo.). In some embodiments, the relaxin is a H2 relaxin agonist such as those produced by Compugen (Tel Aviv, Israel). In other less preferred embodiments, the relaxin is H1 human relaxin, or H3 human relaxin. Relaxin can be administered to the subject in an amount of about 10 µg/kg to about 100 µg/kg of subject body weight per day once the deficiency is determined. In one preferred embodiment, relaxin is administered to the subject in an amount of about 30 µg/kg of subject body weight per day throughout gestation or throughout a part of gestation. As such, relaxin is administered to the subject so as to maintain, for example, a serum concentration of relaxin of about 10 ng/ml throughout pregnancy. The pharmaceutical formulation of relaxin can be administered subcutaneously (SQ) or through other routes.

The beneficial effect of administering relaxin to a pregnant human female is believed to be a direct result of relaxin acting as a receptor-specific agent that stimulates both angiogenesis and vasodilation. Increasing angiogenesis targets the cause for preeclampsia, namely an insufficient blood supply from mother to child which eventually leads to a dangerously high blood pressure in the mother. Increasing vasodilation further assists with reducing blood pressure as well as increasing renal blood flow in the kidney which further reduces the symptoms of preeclampsia. Thus, when the pregnant human female receives a pharmaceutical composition with pharmaceutically active relaxin or pharmaceutically effective relaxin agonist which targets specific relaxin receptors (e.g., LRG7, LGR8, GPCR135, GPCR142 receptors) the result is amelioration or prevention of preeclampsia.

Enriched Human Population

One advantage of early detection is to enrich a group of women more likely to get the disease for research studies and/or clinical studies and to facilitate testing of prophylatic measures. The present disclosure allows for a novel screening process which includes the selection of an enriched population of patients for clinical and/or research studies to better understand preeclampsia and the disease progress and ways to combat it. The enriched population of women can be defined through testing for low relaxin levels wherein many fewer patients are needed in order to achieve scientifically and/or clinically relevant results. Pregnant women in the first or second trimester of pregnancy or prior to manifestation of preeclampsia symptoms can be tested for relaxin levels in the blood stream and those with a level of relaxin of less then about 500 pg/ml are selected for the enriched patient population. Without this valuable selection process, it would require the screening of hundreds of women in order to determine whether a new drug or agent has an effect on preeclampsia. Thus, the disclosure provides a method of screening for novel agents to treat or prevent preeclampsia during a clinical and/or research study, including selecting pregnant women who have a higher likelihood of developing preeclampsia from an enriched population and testing these women for effectiveness of the novel agents. The enriched population includes women in the first and second trimester of pregnancy or prior to manifestation of preeclampsia symptoms with a relaxin level in the blood stream that is less then about 500 pg/ml.

Relaxin Compositions and Formulations

Relaxin, relaxin agonists, relaxin mimetics and/or relaxin analogs are formulated as pharmaceuticals to be used in the methods of the disclosure. Any composition or compound that can stimulate a biological response associated with the binding of biologically or pharmaceutically active relaxin (e.g., synthetic relaxin, recombinant relaxin) or a relaxin agonist (e.g., relaxin analog or relaxin-like modulator or relaxin mimetic) to relaxin receptors can be used as a pharmaceutical in the disclosure. General details on techniques for formulation and administration are well described in the scientific literature (see *Remington's Pharmaceutical Sciences*, Maack Publishing Co, Easton Pa.). Pharmaceutical formulations containing pharmaceutically active relaxin can be prepared according to any method known in the art for the manufacture of pharmaceuticals. The formulations containing pharmaceutically active relaxin or relaxin agonists used in the methods of the disclosure can be formulated for administration in any conventionally acceptable way including, but not limited to subcutaneously (SQ), intramuscularly, intravenously, sublingually, topically, orally and via inhalation. Illustrative examples are set forth below. In one preferred embodiment, relaxin is administered subcutaneously (SQ).

When the drugs are delivered subcutaneously (SQ), the formulations containing pharmaceutically active relaxin or a pharmaceutically effective relaxin agonist can be in the form of a sterile injectable preparation, such as a sterile injectable aqueous or oleaginous suspension. For example, relaxin can be diluted in sodium acetate at pH 5.0 where it is very soluble and stable. Patients can be treated with a relaxin composition via continues infusion as long as necessary. For example, relaxin infusion pumps deliver relaxin through a cannula to a needle that is applied subcutaneously and the pumps can be worn on a belt under the patient's clothes. Relaxin can also be administered via timely relaxin injections while the patient is being monitored for symptoms of preeclampsia. Doses can be adjusted on a patient by patient basis.

Relaxin suspensions can be formulated according to the known art using those suitable dispersing or wetting agents and suspending agents which have been mentioned above. The sterile injectable preparation can also be a sterile injectable solution or suspension in a nontoxic parenterally-acceptable diluent or solvent. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

Aqueous suspensions of the disclosure contain relaxin in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending relaxin in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

Dispersible powders and granules of the disclosure suitable for preparation of an aqueous suspension by the addition of water can be formulated from relaxin in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical formulations of the disclosure can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

Administration and Dosing Regimen of Relaxin Formulations

The formulations containing pharmaceutically active H2 relaxin or a pharmaceutically effective H2 relaxin chimera, agonist, or mimetic used in the methods of the disclosure can be administered in any conventionally acceptable way including, but not limited to, subcutaneously, intramuscularly, intravenously, sublingually, topically, orally and via inhalation. Administration will vary with the pharmacokinetics and other properties of the drugs and the patients' condition of health. General guidelines are presented below.

The methods of the disclosure reduce the likelihood of the development of preeclampsia in pregnant women. The amount of relaxin alone or in combination with another agent or drug that is adequate to accomplish this is considered the therapeutically effective dose. The dosage schedule and amounts effective for this use, i.e., the "dosing regimen," will depend upon a variety of factors, including the general state of the patient's health, the patient's physical status, the type of pregnancy (e.g., single vs. multiple pregnancy) age, and the like. In calculating the dosage regimen for a patient, the mode of administration is also taken into consideration. The dosage regimen must also take into consideration the pharmacokinetics, i.e., the rate of absorption, bioavailability, metabolism, clearance, and the like. Based on those principles, relaxin can be used to reduce or prevent development of preeclampsia in pregnant women. The disclosure also provides relaxin or a relaxin agonist or mimetic and, optionally, another drug for simultaneous, separate or sequential administration. For example, the disclosure provides relaxin and, optionally, a hypertensive medication for combined use in therapy if needed. In another example, the disclosure further provides relaxin and, optionally, $MgSO_4$ for seizure prophylaxis in combined therapy.

The disclosure also provides the use of relaxin in the manufacture of a medicament for reducing or preventing the development of preeclampsia in pregnant women. As such, the medicament is prepared for administration during pregnancy. The disclosure further provides relaxin or a relaxin analog or mimetic for use in a method of reducing the likelihood of the development of preeclampsia, wherein relaxin is prepared for administration to pregnant women.

The state of the art allows the clinician to determine the dosage regimen of relaxin for each individual pregnant woman. As an illustrative example, the guidelines provided below for relaxin can be used as guidance to determine the dosage regimen, i.e., dose schedule and dosage levels, of formulations containing pharmaceutically active relaxin administered when practicing the methods of the disclosure. As a general guideline, it is expected that the daily dose of pharmaceutically active H1, H2 and/or H3 human relaxin (e.g., synthetic, recombinant, analog, agonist, mimetic, etc.) is typically in an amount in a range of about 10 to about 100 µg/kg of subject body weight per day. In one preferred embodiment, the dosage of relaxin is 30 µg/kg/day throughout gestation. In another embodiment, these dosages result, for example, in serum concentrations of relaxin of about 10 ng/ml. In one preferred embodiment, pharmaceutically effective relaxin or an agonist thereof is administered at about 30 µg/kg/day throughout gestation or throughout a part of gestation. In another preferred embodiment, pharmaceutically effective relaxin or an agonist thereof is administered at about 10 to about 100 µg/kg/day throughout gestation or throughout a part of gestation. In another embodiment, the administration of relaxin is continued as to maintain a serum concentration of relaxin of from about 0.5 to about 300 ng/ml, more preferably from about 0.5 to about 100 ng/ml, and most preferably from about 0.5 to about 10 ng/ml. Most preferably, the administration of relaxin is continued as to maintain a serum concentration of relaxin of 10 ng/ml or greater throughout pregnancy. These relaxin concentrations can reduce the likelihood of the development of preeclampsia and with it, symptoms in the mother such as hypertension, high blood pressure, proteinuria, renal insufficiency and mortality. Furthermore, these relaxin concentrations can reduce or prevent the likelihood of low birth weight in infants and associated risks as well as infant deaths. Depending on the subject, the relaxin administration is maintained for as specific period of time or for as long as needed to achieve stability in the pregnant mother and child. For example, relaxin can be administered through continuous infusion through the end of gestation. This can be achieved via an infusion pump or other means. Alternatively, relaxin can be administered during the first and/or second trimester only if needed.

Relaxin-Specific and CRP-Specific Antibodies

Described herein are methods for the production of antibodies capable of specifically recognizing epitopes of relaxin and/or CRP. Such antibodies can include, but are not limited to, polyclonal antibodies, monoclonal antibodies (mAbs), human, humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. For the production of antibodies to relaxin and/or CRP, various host animals can be immunized by injection with a relaxin protein or a CRP protein, or a portion of either. Such host animals can include, but are not limited to rabbits, mice, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as relaxin or CRP, or an antigenic functional derivative of relaxin or CRP. For the production of polyclonal antibodies, host animals such as those described above, can be immunized by injection of relaxin or CRP. The antibody titer in the immunized animal can be monitored over time by standard techniques, such as with an enzyme linked immunosorbent assay (ELISA) using immobilized polypeptide. If desired, the antibody molecules can be isolated from the animal (e.g., from the blood) and further purified by well-known techniques, such as protein A chromatography to obtain the IgG fraction. Monoclonal antibodies, which are homogeneous populations of antibodies to a particular antigen such as relaxin or CRP, can be obtained by any technique which provides for the production of antibody molecules by continuous cell lines in culture which are well known in the art. Such antibodies can be of any immunoglobulin class including IgG, IgM, IgE, IgA, IgD and any subclass thereof. The hybridoma producing the mAb of this disclosure can be cultivated in vitro or in vivo.

Alternative to preparing monoclonal antibody-secreting hybridomas, a monoclonal antibody directed against relaxin and/or CRP can be identified and isolated by screening a recombinant combinatorial immunoglobulin library (e.g., an antibody phage display library) with relaxin, CRP or derivates thereof. Kits for generating and screening phage display libraries are commercially available. Additionally, recombinant antibodies, such as chimeric and humanized monoclonal antibodies, comprising both human and non-human portions, which can be made using standard recombinant DNA techniques, are within the scope of the disclosure. A chimeric antibody is a molecule in which different portions are derived from different animal species, such as those having a variable region derived from a murine mAb and a human immunoglobulin constant region (e.g., U.S. Pat. Nos. 4,816,567 and 4,816,397). Humanized antibodies are antibody molecules from non-human species having one or more complementarily determining regions (CDRs) from the non-human species and a framework region from a human immunoglobulin molecule (e.g., U.S. Pat. No. 5,585,089). Such chimeric and humanized monoclonal antibodies can be produced by recombinant DNA techniques known in the art.

The antibodies described herein can be used in any assay where the blood of pregnant women is tested for relaxin levels in order to determine if the women are at a higher risk of developing preeclampsia than their healthy counterparts. If relaxin levels in the blood fall below of about 500 pg/ml then the women are at a higher risk for developing preeclampsia and need to be carefully monitored and/or treated with relaxin during all or part of gestation. Optionally, the blood of pregnant women can further be tested for CRP levels in order to achieve a more sensitive assay. If CRP levels in the blood are below 1.5 mcg/ml or above 13.5 mcg/ml then the women are even more likely to develop preeclampsia. Any assay that allows for the accurate determination of relaxin and/or CRP levels in blood can be employed herein, including, ELISA, bio assays, immune assays and others. Commercially available kits may also be employed.

EXPERIMENTAL

The following abbreviations are used herein: mcg or μg (microgram); ml (milliliter); pg (picogram); BMI (body mass index); CART (classification and regression tree); CI (confidence interval); CREAT (creatinine); CRP (C-reactive protein); ELISA (enzyme-linked immunosorbent assay); HP (hypertension, proteinuria); HPU (hypertension, proteinuria, uric acid); HU (hypertension, uric acid); Rlx or RLX (relaxin).

The following specific examples are intended to illustrate the disclosure and should not be construed as limiting the scope of the claims.

Example 1

Study of Preeclamptic Pregnant Women

Relaxin, a peptide hormone released from the corpus luteum of the ovary, is a potent vasodilator in pregnancy. Serum H2 concentrations rise during the first trimester and peak in the early second trimester coinciding with marked maternal renal and systemic vasodilation. In contrast, inadequate vasodilatory adaptation and increased systemic vascular resistance are hallmarks of preeclampsia. This example describes the measurement of serum relaxin during pregnancy and determination of an association of reduced serum relaxin during the first trimester with an increased risk of developing preeclampsia.

A nested case-control study of 62 women of less than 13 weeks' gestation was conducted. Of the 62 study subjects, 37 women developed preeclampsia, as defined by new onset of hypertension and proteinuria after 20 weeks' gestation. The remaining subjects were normotensive and had uncomplicated pregnancies. H2 relaxin was measured by ELISA (although other assays are also suitable for this purpose, such as bioassay, RT-PCR, etc.). Descriptive statistics including logistic regression were used for data analysis.

Specifically, the concentration of human relaxin 2 in serum was measured by immunoassay, using R&D Systems Analytical Testing Service (Minneapolis, Minn.). The H2 relaxin-specific monoclonal antibody employed in this immunoassay was a mouse IgG1 produced by the 3F2.F2 hybridoma. The 3F2.F2 hybridoma was developed by BAS Medical, now Corthera Inc. (San Mateo, Calif.), and was deposited under the Budapest Treaty as American Type Culture Collection (ATCC, Manassas, Va.) Patent Deposit Designation PTA-8423. The H2 relaxin ELISA employing the 3F2.F2 antibody was well validated. No significant cross-reactivity or interference was observed with recombinant human IGF-1, IGF-II, insulin (amino acids 25-100), insulin-like 3, relaxin 1 (H1) and relaxin 3 (H3). In addition, no significant cross-reactivity or interference was observed with recombinant canine, porcine or rodent (mouse and rat) relaxin-2.

Serum relaxin concentrations were not significantly different between preeclamptic women and controls (median and interquartile ranges, 670.4 [456.9-1117.2] vs. 802.3 [570.8-966.4] pg/ml, p=0.47). However, women with relaxin concentrations less than 477 pg/ml, a cutoff that approximates the lowest quartile, had an odds ratio of 6.2 (95% CI 1.3-30.7, p=0.025) for developing preeclampsia. After adjusting for gestational age at sample collection, body mass index (BMI), race, and smoking status, these women were 7.4 times more likely to develop preeclampsia (95% CI 1.4-38.9, p=0.02), which was surprisingly high. This strong association persisted in a subgroup of women with new onset hypertension, proteinuria, and hyperuricemia, a more homogeneous preeclamptic subset with higher rate of adverse outcomes (adjusted OR 6.9, 95% CI 1.2-40, p=0.03).

This study indicates that a low serum relaxin concentration is an independent risk factor for preeclampsia. Inadequate vasodilatory adaptations secondary to relaxin deficiency in early pregnancy may further contribute to the pathogenesis of preeclampsia.

Example 2

Statistical Analysis of Preeclampsia Prediction

CART (classification and regression tree) was used to analyze data obtained from 69 pregnant women having characteristics shown in Table 2. This expanded analysis was based on data obtained from the original study subjects of Example 1, as well as several additional subjects. The parameters used for preeclampsia prediction were H2 relaxin levels first, and then also C-reactive protein (CRP) levels. As can be seen in FIG. 1, the gestational age during pregnancy was broken down into three periods, i.e., 0-15 weeks (first trimester), 15-25 weeks (second trimester), and 25-35 weeks (third trimester). FIG. 1 depicts serum relaxin concentrations in preeclamptic women (HPU and HP groups) with respect to gestational age. The lines connect samples from the same subject. The triangles depict samples from pregnant women who later developed preeclampsia and had endogenous H2 relaxin levels below 500 pg/ml in the first 15 weeks. The squares depict samples from pregnant women who later developed preeclampsia but had endogenous H2 relaxin levels of about 500 pg/ml. The diamonds depict samples from pregnant women who did not develop preeclampsia. It should be noted that few of these women had H2 relaxin concentrations in the first 15 weeks that were below 500 pg/ml.

TABLE 2

Characteristics of Pregnant Subjects

| Category | Total | Caucasian | African American |
|---|---|---|---|
| HP | 15 | 11 | 4 |
| HPU | 19 | 12 | 7 |
| HU | 10 | 6 | 4 |
| Normal | 25 | 16 | 9 |
| Grand Total | 69 | 45 | 24 |

In the CART analysis, all samples from a subject during the first 15 weeks were averaged. This is because there were different numbers of samples collected and at different times during gestation for each subject. Referring to the classification tree of FIG. 3, the number of splits was one, and the number of terminal nodes was two. More specifically, the top box shows that there were 35 preeclamptic subjects with natural H2 relaxin levels below 476.7 pg/ml (see dashed bar) and 24 normal subjects with natural H2 relaxin levels above 476.7 pg/ml (see solid lined bar). In order to further determine the specificity of the relaxin test, the preeclamptic and normal subjects were split into two groups, Box 2 on the left shows those subjects with less than or equal to 476.7 pg/ml serum H2 relaxin and Box 3 on the right shows those subjects with greater than 476.7 pg/ml serum H2 relaxin. As can be seen in Box 2 on the left, out of those with H2 relaxin levels less than or equal to 476.7 pg/ml relaxin, 13 individuals developed preeclampsia while only one individual had a normal pregnancy making this test highly specific. As can be seen in Box 3 on the right, out of those with H2 relaxin levels above 476.7 pg/ml, 23 individuals had a normal pregnancy and 22 individuals developed preeclampsia. The results shown in Box 3 on the right prompted the inclusion of a second parameter to increase the sensitivity of the test.

FIG. 4 shows the same classification tree as in FIG. 3, plus a further split based on C-reactive protein (CRP) levels. Subjects with H2 relaxin levels above 476.7 were split into those with CRP levels less than or equal to 13.481 mcg/ml and those with CRP levels above 13.481 mcg/ml. Noticeably, those women with CRP levels above 13.81 mcg/ml are very likely to develop preeclampsia, which is shown in Box 5 representing nine pregnant women that developed preeclampsia and one pregnant woman that had a normal pregnancy. Box 4 was further split into those with CRP levels less than or equal to 1.4681 mcg/ml and those with CRP levels above 1.4681 mcg/ml. As can be seen in Box 6, seven individuals developed preeclampsia while only one individual had a normal pregnancy, making this test more sensitive. By employing a CRP measurement, the sensitivity of the test was increased to 83 percent.

Figure 5:
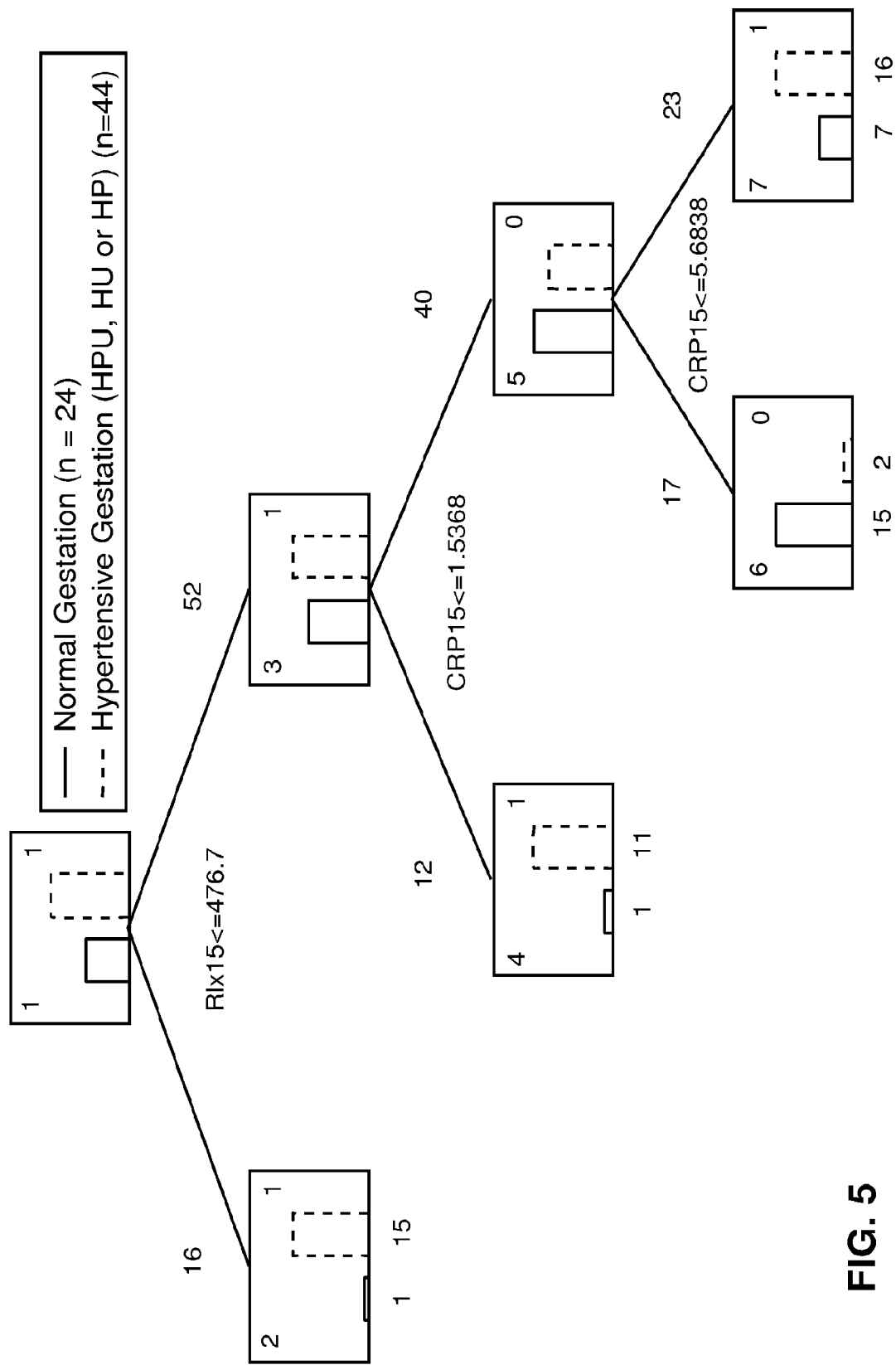
FIG. 5 shows a classification tree for HPU, HU or HP gestations (i.e., hypertensive women including preeclamptic women), in which the number of splits is three and the number of terminal nodes is four. With relaxin (Rlx) and C-reactive protein (CRP) measurements the specificity is 63% and the sensitivity is 96%.

FIG. 5 shows a classification tree for hypertensive gestations (HP, HPU and HU subjects, see also Tables 1 and 2). The subjects were split into four groups based serum H2 relaxin and CRP concentrations during early gestation. Through the use of these two measurements, a very good sensitivity level was obtained. In fact, employing both relaxin and CRP measurements, the specificity was 63% and the sensitivity was 96%.

Figure 6:
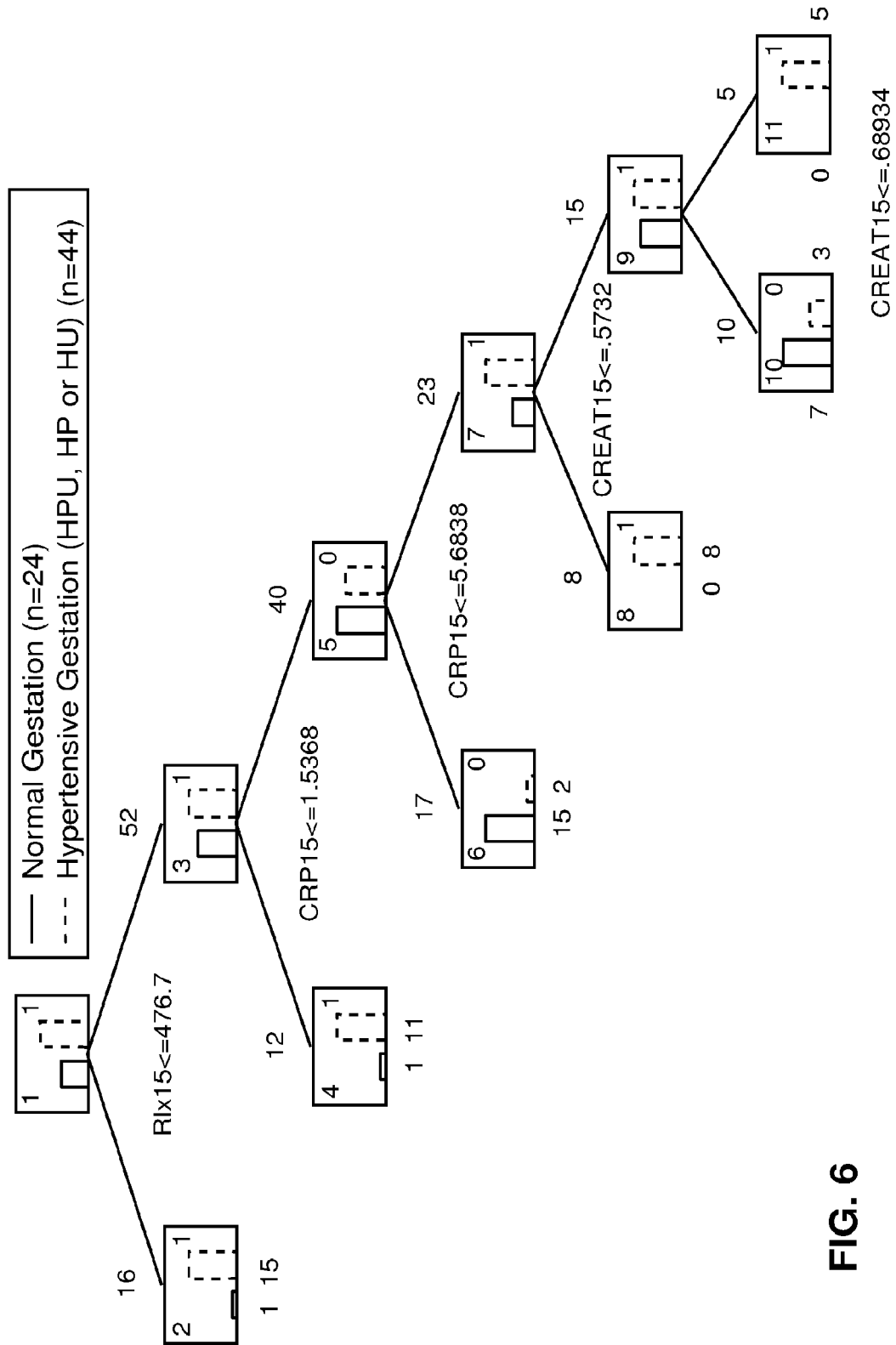
FIG. 6 depicts a classification tree for HPU, HU or HP gestations (i.e., hypertensive women including preeclamptic women), in which the number of splits is five and the number of terminal nodes is six. With relaxin (Rlx), C-reactive protein (CRP), and creatinine (CREAT) measurements the specificity is 92% and the sensitivity is 87%.

FIG. 6 shows another classification tree for hypertensive gestations (i.e., 48 hypertensive women including HP, HPU and HU and 25 normal women). The subjects were split based on serum H2 relaxin and CRP levels as in FIG. 5, as well as on creatinine levels to further refine the prediction. By the use of these three analytes, a very sensitive and specific algorithm for the prediction of pregnancies that will later develop hypertension was developed. With relaxin, CRP, and creatinine (CREAT) the specificity was 92% and the sensitivity was 87%. Since these women were not preeclamptic but only candidates for hypertensive gestation, CREAT was used to determine the likelihood of hypertension in addition to H2 relaxin and CRP.

Example 3

Predicting Preeclampsia in Pregnant Women

A serum sample from a pregnant woman is collected during early gestation. The serum H2 relaxin concentration and the concentration of CRP are determined by ELISA. Using the algorithm as shown in FIG. 3, the likelihood of developing preeclampsia is determined. For example if the serum H2 relaxin level is 300 pg/ml, the patient is placed into treatment to prevent the almost certain development of preeclampsia. If the serum relaxin level is 600 pg/ml, the CRP level is also examined. If the CRP level is greater than 1.5 mcg/ml and less then 13.5 mcg/ml the pregnancy is considered a normal gestation. However if the pregnant subjects' CRP level falls outside of this range, then she has an increased risk of developing preeclampsia.

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are understood by those skilled in the art are intended to be within the scope of the claims.

We claim:

1. A method of assessing whether a pregnant woman has an increased risk of developing preeclampsia, comprising:
    a) obtaining a sample of plasma or serum from a woman during week 5-15 of pregnancy;
    b) measuring the H2 relaxin concentration in the plasma or serum by immunoassay; and
    b) determining that said pregnant woman has an increased risk of developing preeclampsia when said H2 relaxin concentration is less than about 500 pg/ml,
wherein an H2 relaxin concentration of less than about 500 pg/ml is an independent risk factor for preeclampsia.

2. The method of claim 1, wherein said H2 relaxin is measured with an enzyme-linked immunosorbant assay (ELISA).

3. The method of claim 1, wherein said pregnant woman is pregnant for the first time, over 35 years of age, under 18 years of age or is carrying more than one fetus.

4. The method of claim 1, further comprising measuring C-reactive protein (CRP) concentration in the plasma or serum, and determining that said pregnant woman has an increased risk of developing preeclampsia when said CRP concentration is greater than about 13.5 mcg/ml, even when said H2 relaxin concentration is greater than about 500 pg/ml.

5. The method of claim 1, further comprising measuring C-reactive protein (CRP) concentration the plasma or serum, and determining that said pregnant woman has an increased risk of developing preeclampsia when said CRP concentration is less than about 1.5 mcg/ml, when said H2 relaxin concentration is greater than about 500 pg/ml.

* * * * *

UNITED STATES PATENT AND TRADEMARK OFFICE
CERTIFICATE OF CORRECTION

PATENT NO. : 8,574,851 B2
APPLICATION NO. : 13/129597
DATED : November 5, 2013
INVENTOR(S) : Dennis R. Stewart, Kirk Conrad and Arundhathi Jeyabalan It is certified that error appears in the above-identified patent and that said Letters Patent is hereby corrected as shown below:

In the specification

In Column 1, line 25, please insert the following:

--STATEMENT REGARDING FEDERALLY SPONSORED RESEARCH
This invention was made with Government support under HD030367 and HL067937 awarded by the National Institute of Health. The Government has certain rights in this invention.--

Signed and Sealed this
Ninth Day of August, 2016

Michelle K. Lee
*Director of the United States Patent and Trademark Office*